United States Patent
Rueter

(10) Patent No.: US 7,400,924 B2
(45) Date of Patent: Jul. 15, 2008

(54) SYSTEM AND METHOD FOR CAPTURE MANAGEMENT

(75) Inventor: John C. Rueter, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 505 days.

(21) Appl. No.: 11/114,463

(22) Filed: Apr. 26, 2005

(65) Prior Publication Data

US 2006/0241710 A1    Oct. 26, 2006

(51) Int. Cl.
*A61N 1/37* (2006.01)

(52) U.S. Cl. .......................... 607/28; 607/27

(58) Field of Classification Search ............ 607/27, 607/28
See application file for complete search history.

(56) References Cited

U.S. PATENT DOCUMENTS

| 4,953,551 | A | 9/1990 | Mehra et al. ............ 128/419 D |
| 5,117,824 | A | 6/1992 | Keimel et al. ............ 128/419 D |
| 5,163,427 | A | 11/1992 | Keimel .................... 128/419 D |
| 5,188,105 | A | 2/1993 | Keimel .................... 128/419 D |
| 5,601,615 | A | 2/1997 | Markowitz et al. ............ 607/28 |
| 5,871,512 | A | 2/1999 | Hemming et al. ............. 607/28 |
| 5,954,755 | A | 9/1999 | Casavant ..................... 607/28 |
| 6,477,422 | B1 | 11/2002 | Splett ......................... 607/28 |
| 6,618,619 | B1 * | 9/2003 | Florio et al. .................. 607/27 |
| 6,947,794 | B1 * | 9/2005 | Levine ........................ 607/28 |
| 2003/0083708 | A1 * | 5/2003 | Bradley et al. ............... 607/27 |
| 2004/0064162 | A1 * | 4/2004 | Manrodt et al. .............. 607/28 |

FOREIGN PATENT DOCUMENTS

EP    1 184 050 A2    3/2002

* cited by examiner

*Primary Examiner*—Carl H. Layno
*Assistant Examiner*—Eugene T Wu
(74) *Attorney, Agent, or Firm*—Daniel G. Chapik

(57) ABSTRACT

An implantable medical device (IMD) includes both evoked response and algorithmic based threshold testing methodologies. The leads used with the IMD are evaluated to determine whether they are high or low polarization. The evoked response methodology is only utilized if the leads are low polarization.

12 Claims, 5 Drawing Sheets

SYSTEM AND METHOD FOR CAPTURE MANAGEMENT

FIELD OF THE INVENTION

The present invention relates to medical devices and more specifically, medical devices that deliver electrical stimulation.

DESCRIPTION OF THE RELATED ART

Various devices exist that deliver electrical stimulation as a therapy. Such a therapy might include cardiac pacing, cardioversion, and/or defibrillation via an implantable or an external device. Alternatively, electrical stimulation may be delivered to another anatomical structure to affect a neurological, nervous, musculature, gastrointestinal, auditory, optical/visual, or other response or therapy. Thus, while the present invention is discussed in the context of an implantable medical device providing cardiac pacing, it should be appreciated that the invention is not so limited and is applicable to a variety of implantable and external devices that deliver electrical stimulation.

When providing cardiac pacing, an electrical stimulus is delivered to a targeted area of cardiac tissue. For example, a lead may be positioned such that an electrode is in contact with a portion of the atrium to provide atrial pacing, effectively replacing the SA node on a permanent or selective basis. Similarly, a lead may be positioned such that an electrode contacts e.g., the apex of the right ventricle, some portion of the HIS bundle, the cardiac vein, etc. to provide ventricular pacing. Leads and electrodes may be positioned endocardially, epicardially, subcutaneously, or may be surface mounted.

In any event, an electrical pulse is generated and "captures" the cardiac cells, initiating a depolarization wave that progresses along the conduction pathway. As is well known, such a pulse may be delivered to the atrium for atrial pacing and various locations subsequent (electrically) to the AV node for ventricular pacing. In order to successfully capture, the electrical pulse must exceed a threshold with an appropriate combination of amplitude (strength) and pulse width (duration). This threshold will vary from patient to patient and may also vary over time within a given patient. Sub-threshold pulses will generally not capture the heart.

Thus, this is but one motivating factor to increase the amplitude and/or pulse width of the pacing pulse to assure capture. Opposing factors include conserving battery life and limiting the pulse width to within the normal timing parameters of the standard events of the cardiac cycle. Therefore, at least in implantable devices having a battery, the pacing pulses are set at or near the threshold requirements. Typically, there is a safety margin that is added to (or a multiplicative factor) the pacing pulse in excess of the determined threshold.

As indicated, threshold levels vary from patient to patient and depend on a large number of factors, some of which may be time varying. Threshold levels are measured for each patient and the pacing parameters are programmed accordingly. This is, of course, done at the time of implant, but is also periodically done during follow up visits, either in-office or remotely. Furthermore, there are devices that have the capability to perform threshold testing and either report the results or automatically adjust the pacing parameters accordingly. For example, U.S. Pat. Nos. 5,601,615; 5,871,512; 5,954,755; and 6,477,422, all assigned to Medtronic, Inc. illustrate various capture techniques and are herein incorporated by reference in their entireties

DETAILED DESCRIPTION

Figure 1:
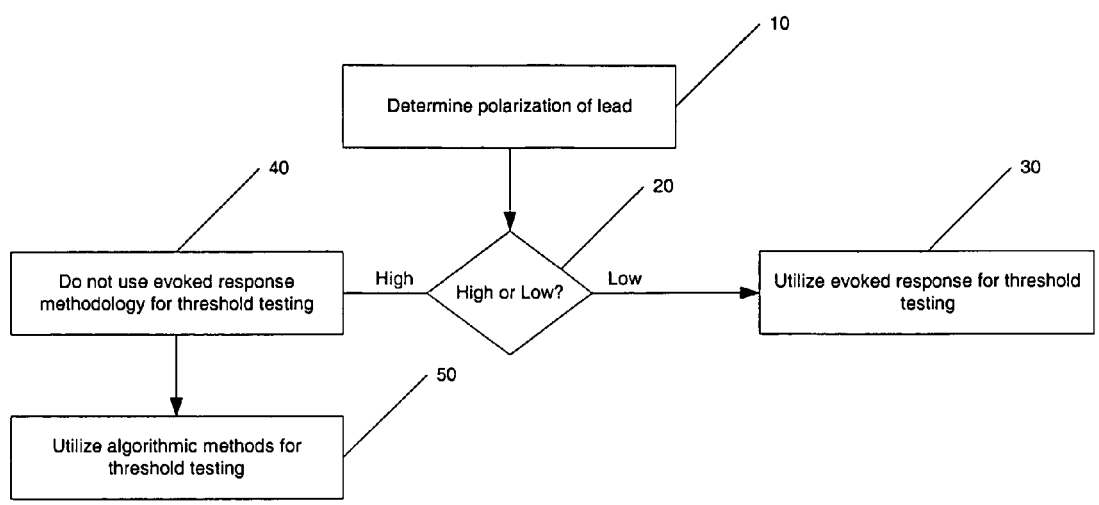
FIG. 1 is a flowchart illustrating a process for determining a threshold testing protocol.

As indicated by the above referenced documents, there are a variety of capture management protocols that are referred to herein as algorithmic based. In one methodology, atrial pacing is provided and the ventricular response is sensed. That is, if the atrial pace captures the atrium; the ventricle should depolarize within a predetermined period of time if the patient has intact conduction. If the ventricular event occurs outside of this window, the methodology indicates that the atrial pace failed to capture. Where the patient does not have intact conduction but does have a relatively reliable underlying rhythm, then pacing pulses are delivered prematurely; that is, prior to the anticipated intrinsic event. If the intrinsic event still occurs, the pacing pulse failed to capture. Similar approaches may be utilized in both the atrium and ventricles.

Many variations of the algorithmic capture management protocols exist and may be employed under the supervision of a caregiver. That is, the threshold testing may be done in-office or remotely by utilizing a medical device programmer in communication with the medical device. Alternatively, the implanted device may perform the threshold testing in an automated fashion. In either case, threshold testing is performed on a periodic basis. When only in-office visits are utilized, such testing may be relatively infrequent, e.g., monthly, quarterly, semi-annually, etc. With the automated capability, threshold testing is typically performed on a daily basis.

With periodic testing, the threshold is determined and a safety margin is provided to account for any changes that might occur in the interval before the subsequent test. That is, if the pacing parameters were set to the exact threshold levels measured during a first threshold test, the patient's threshold could increase and the delivered pacing pulses would then be sub-threshold. As such, the threshold is determined and a safety margin is added. The safety margin may be a fixed quantity or may be a multiplicative factor. In this manner, pacing is occurring at a level (amplitude and/or pulse width) that is greater than actually required to capture. While such a safety margin is often prudent, providing a pacing stimulus higher than what is actually required at least marginally diminishes battery longevity.

As an alternative to the algorithmic based capture management options, the device measures an evoked response after the pacing stimulus is delivered. In this methodology, the electrical depolarization of the cardiac tissue is sensed directly and is evidence that the pacing pulse captured. With this methodology, capture may be determined after every delivered pacing stimulus; thus, if there is a loss of capture then the stimulus can be immediately modified. This is often referred to as threshold testing or capture detection on a beat-to-beat or continual basis. One difficulty with this approach is measuring a relatively small signal, in a narrow and specific time window, with an electrode that is affected by the comparatively large pacing stimulus that had just been delivered.

Measuring or detecting an evoked response is currently not feasible with a lead/electrode that has a "high" polarization. Depending upon the electrode configuration, charge or potential remains on the electrode for a period of time after delivering the stimulus. Thus, if this electrode is used to sense the evoked response and the polarization level is high, the device will likely sense or measure the effects of lead polarization rather than the evoked response. The period of time during which the evoked response needs to be sensed corresponds to when polarization occurs. Thus, if a high polarization electrode is used to attempt to sense an evoked response, the device will likely incorrectly attribute the sensed signal to an evoked response and hence indicate capture regardless of whether capture actually occurs.

Thus, with respect to the present invention and absent any means to dissipate the accumulated potential, provided alternative sensing mechanisms, or discriminate between the electrode polarization and the evoked response, the evoked response methodology is preferably not used as a basis for threshold testing for leads that are high polarization.

There is no generally accepted industry standardization or quantification of lead polarization. Functionally, and as used herein, a lead or electrode having high polarization is such that the level of polarization after delivering a pacing pulse precludes a reliable measurement of an evoked response whereas a low polarization lead or electrode has a level of polarization that is sufficiently low to permit an evoked response to be sensed with an acceptable level reliability.

Prior to implantation, lead polarization may be empirically measured. For example, the lead is placed in a saline solution and a pacing pulse or test stimulus is delivered. The potential on the lead post stimulus is measured (e.g., a voltage) at a given time or during a given time interval. This measurement may be used to determine whether a lead has high or low polarization and may be used to compare one brand, type or style of lead to another or to compare a given lead to a reference value. Post implant, there are various methodologies that may be employed to measure lead polarization.

FIG. 1 is a flowchart illustrating process for selecting pacing threshold methodologies. Initially, the lead or leads at issue are analyzed (10) to determine if they are high polarization or low polarization leads. As indicated, this determination may be made by measuring a parameter(s) prior to implant, measuring a parameter(s) after the lead is implanted, or by utilizing a look-up function. That is, various leads may be categorized as high or low polarization and thus, by knowing the type of lead in use, the polarization level is acquired. Of course, by making a measurement, the specific lead is quantified rather than relying upon a generalized categorization.

If the lead is determined (20) to have low polarization, then threshold testing utilizing an evoked response methodology (30) is permitted. Conversely, if the lead has high polarization (20), then threshold testing utilizing the evoked response methodology is precluded (40). Algorithmic based capture management protocols are utilized (50) for threshold testing.

Figure 2:
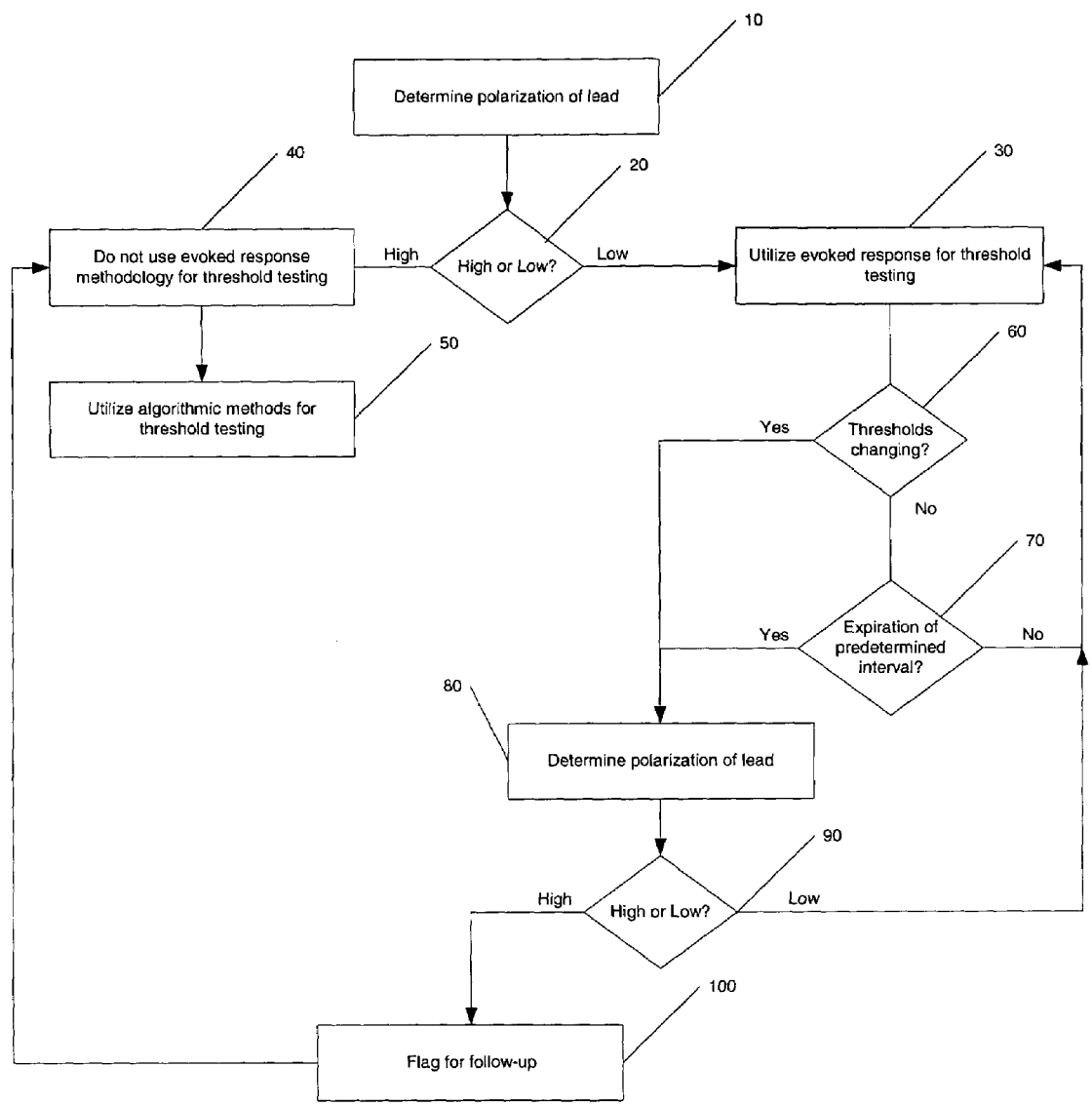
FIG. 2 is a flowchart illustrating a variation of the process of FIG. 1.

FIG. 2 illustrates a process similar to that of FIG. 1. If the lead is determined (20) to have low polarization and an evoked response methodology is used, the device monitors the values obtained as the pacing threshold (which may occur continuously or on a beat-to-beat basis). The device determines (60) whether the threshold values are changing or are changing beyond some predetermined amount to allow for normal variations. Assuming the threshold values are consistent, the device then determines if an evoked response evaluation interval (predetermined interval) has expired (70). The evoked response evaluation interval establishes a frequency of determining whether the evoked response methodology continues to be appropriate for the lead in use. This interval may be set as desired, but will typically be on the order of 24 hours to one week. If the interval has not expired, the process returns to (30) where the evoked response methodology continues to be utilized.

If the threshold values change (60) or the interval expires (70), then the device reevaluates (80) the polarization of the lead. This may take the form of an automated analysis such as measuring a parameter, such as voltage, at an electrode. Alternatively, a caregiver utilizing external instruments may perform the reevaluation. If the determination (90) indicates that the lead continues to have low polarization, then the process returns to utilizing (30) the evoked response methodology and the evoked response evaluation interval is reset.

If the determination (90) indicates that the lead has a high polarization, then the evoked response methodology is no longer utilized (40) and the algorithmic threshold testing is employed (50) exclusively. In addition, a flag (100) is set for follow-up. This flag may take many forms. For example, a parameter may be stored that is recognized during a subsequent interrogation of the implantable device via a medical device programmer (in-office or remotely). Alternatively, a patient warning may be delivered indicating that the patient should have such an interrogation performed (in-office or remotely). The device could also initiate a communication session that results in a full interrogation or alternatively, in a message regarding the polarization change being sent to a caregiver.

In some embodiments, the device may not have a mechanism for measuring lead polarization. Thus, there would not be an evoked response evaluation interval internal to the device. If threshold values change greatly, change in unexpected or unusual ways, fluctuate outside of normal values, or other evidence exists that the device is not appropriately capturing with the levels being indicated, the device may operate under the assumption that the polarization has changed and act accordingly; at least until the appropriateness of utilizing an evoked response methodology can be confirmed.

Assuming that a low polarization lead is provided, a later determination that this lead has high polarization has clinical significance. That is, a change from low to high polarization is likely indicative of some lead malfunction. For example, the lead integrity may have been compromised such as with a fracture, insulation degradation, fluid intrusion, or the like. Thus, this change may in fact be evidence of impending lead failure and would permit corrective action to be taken proactively. Furthermore, polarization changes may be one the earliest detectable parameters indicative of such failure.

The flag 100 would present this indication to the caregiver. As a diagnostic tool, the actual polarization values can be output; however, it would likely be more apparent to have a representative indicator such as a polarization trend, polarization crossing a threshold (low to high), an alert or warning of possible lead failure displayed textually or graphically, or some other display or alert mechanisms to highlight the potential importance of this change to the caregiver and/or the patient.

Figure 3:
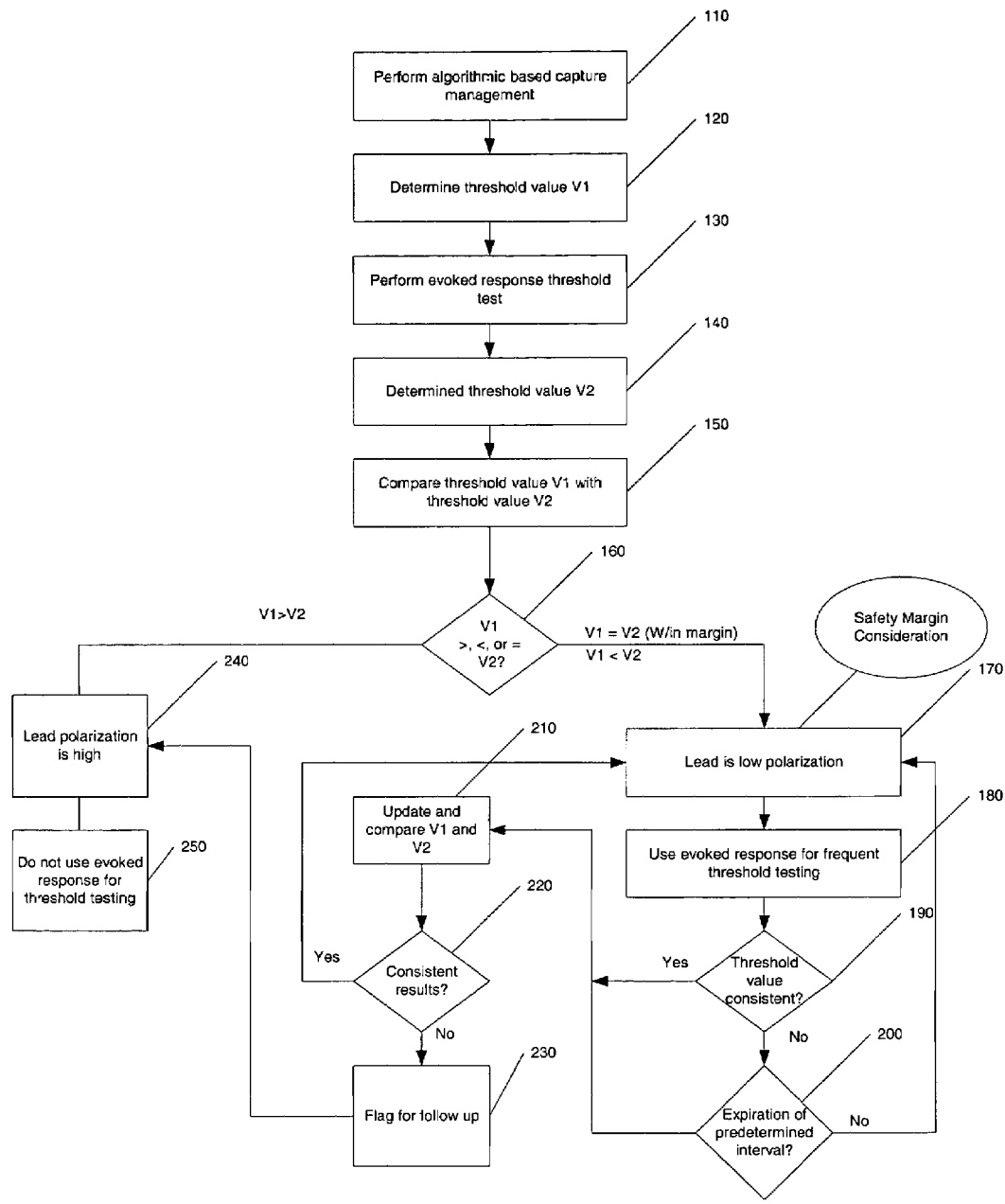
FIG. 3 is a flowchart illustrating a process for utilizing multiple threshold protocol.

FIG. 3 illustrates a process for determining whether an evoked response methodology may be used with a given lead when a direct measurement of polarization is not available. Initially, one or more of the algorithmic capture management methodologies is performed (110) for a given lead or electrode and a threshold value V1 is determined (120). Next, the device senses for evoked responses (130) and attempts to determine (140) a pacing threshold based upon the sensed evoked responses. There may be many reasons why a given device cannot sense an evoked response and a failure to obtain any meaningful data at step (130) may preclude the use of the evoked response methodology, but would not necessarily be indicative of a polarization value. The threshold value obtained from the evoked response methodology is designated V2.

Once both V1 and V2 are obtained, they are compared (150) to one another. Of course, pacing threshold values can include multiple components such as amplitude and pulse width and are simply indicated as a single value (V1, V2) for illustrative purposes. As such, V1 may equal V2 (V1=V2) to within some predetermined tolerance (160), V1 may represent a higher threshold than V2 (V1>V2), or V1 may represent a lower capture threshold than V2 (V1<V2).

If V1 equals V2 (within tolerances) or if V1 is less than V2, then the device determines that the polarization for this lead or electrode is low (170). As such, the evoked response methodology can be utilized (180). One factor to consider is the relevant safety margin. This comparison is done to determine a capture threshold and polarization level. If a safety margin is added, then the higher pacing output could affect lead polarization particularly if the patient's threshold does indeed rise within that safety margin. Thus, it may be desirable to minimize or eliminate the safety margin when utilizing the evoked response methodology. This is generally acceptable, as capture is detected after every pacing pulse; thus, an increase threshold should be immediately determined and accommodated.

Over time, the evoked response methodology is utilized to determine if each pacing pulse captures. The device monitors the thresholds utilized and determines in they are changing (190). Similar to the embodiment of FIG. 2, the device also (optionally) includes an evoked response evaluation interval (predetermined interval). Assuming the threshold values are not changing (beyond normal tolerances) and the interval has not expired, then the process returns to (170) and continues to utilize the evoked response methodology.

Alternatively, if threshold values are have changed or the interval expires, V1 and V2 are updated and compared (210). If the results are consistent (220), then the lead or electrode still has sufficiently low polarization and the process returns to step (170). If the results are not consistent (e.g., V1 is now greater than V2), this fact is flagged for follow up (similar to the previous embodiment) and the process moves to step 240. Here, the device determines that based upon the comparison that the polarization is too high (240) to utilize the evoked response methodology (250) and thus, only the algorithmic capture management protocols are utilized. Similarly, if this same determination is reached at step (160), the process moves to the same conclusion (240). However, as explained above, if a lead or electrode has low polarization and later is indicated to have high polarization, this fact could indicate a lead problem and is flagged accordingly.

At step (220), the values of V1 and V2 are compared and a determination is made as to whether they are consistent. This step may take various forms in alternative embodiments. In one embodiment, steps (210) and (220) are identical to steps (150) and (160). That is, a determination is made as to whether V1 is equal to, greater than or less than V2.

In another embodiment, V1 is compared to V2, but the results are also then compared to the results obtained at step (160) and optionally with results from previous instances of step (220). If V1 is greater than V2, the process will move to step 240 as this indicates that the evoked response methodology is indicating capture at levels below that indicated appropriate by the algorithmic methodologies. This means that is likely that the evoked response methodology is sensing lead polarization and indicated a false capture. No comparison to previous determination is necessary.

If V1 and V2 are substantially equal, then this simply confirms that the evoked response methodology is obtaining the correct results. If V2 is greater than V1, the threshold values are obviously not going to be the same but this indicates that the evoked response methodology is sensing evoked responses and not false positives from lead polarization. If one of these two results is obtained, it can be compared to previous results. For example, if at step (160) V1 and V2 were equal and at step (220) V2 is significantly greater than V1, further analysis may be warranted, despite successfully meeting the criteria for allowing the use of the evoked response methodology. Possible steps might include performing the analysis over and determining if it is anomalous, performing the analysis multiple times and averaging results, or determining if other parameters have changed that might affect the comparison.

If a variation is present, that fact may be noted and provided to the caregiver during the next device communication. The evoked response methodology may continue to be utilized. In one embodiment, the evoked response evaluation interval is shortened to perform more frequent comparisons until a caregiver has evaluated the data. Alternatively, if the discrepancy is sufficiently large, the evoked response methodology may be temporarily suspended, again until caregiver review is achieved. Whether any action and what action is taken based upon a discrepancy between results that does not necessarily indicate high polarization is a programmable parameter that can be set as desired by the caregiver.

In determining the threshold values V1, V2 for the different methodologies, a single value for each may be obtained and utilized. Alternatively, each value may represent a plurality of iterations that are averaged together to minimize the impact of any spurious or anomalous results.

Figure 4:
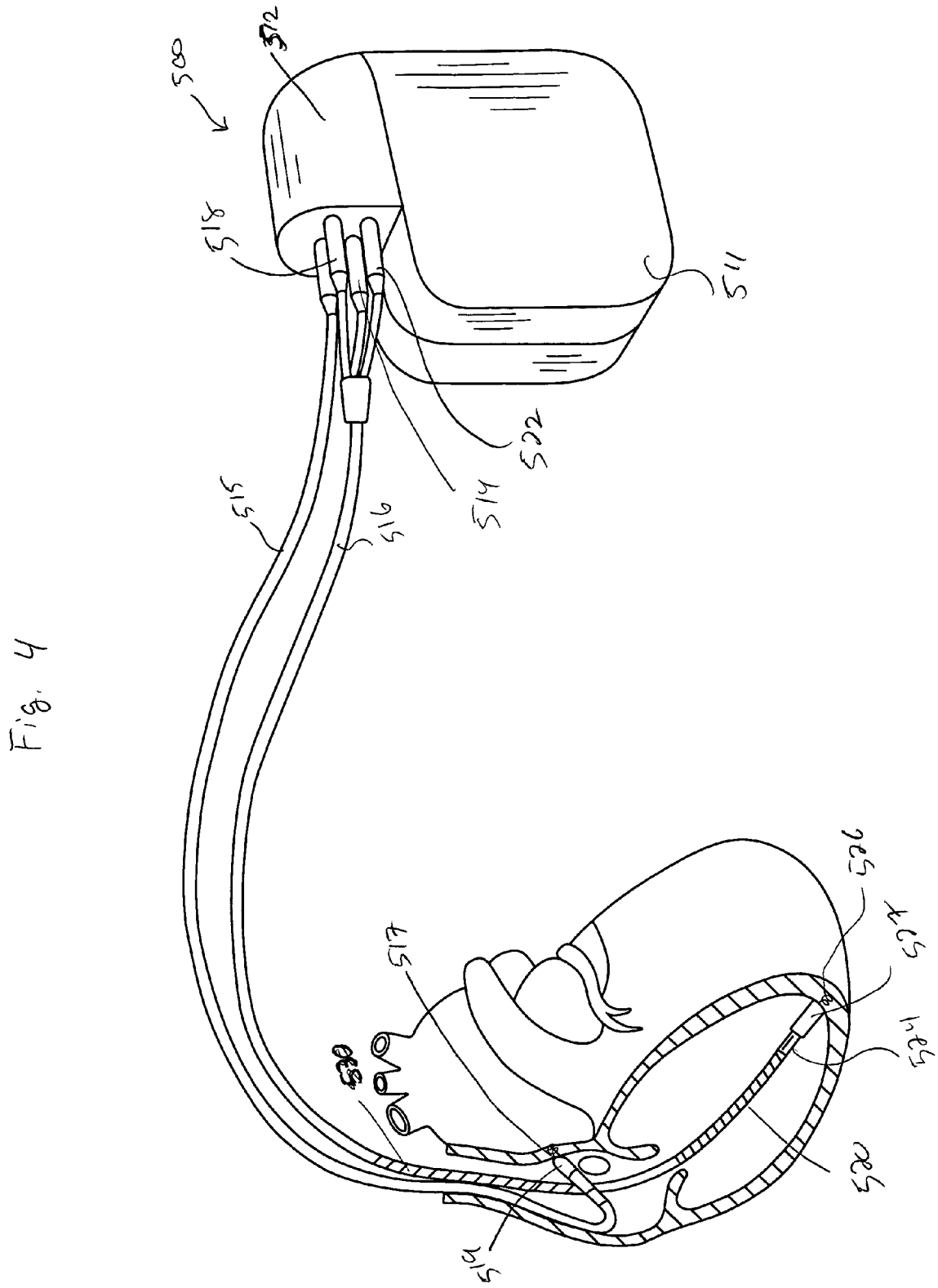
FIG. 4 is an isometric view of an implantable medical device.

Referring now to FIG. 4, there are illustrated an ICD 500 and leads 515 and 516, making up an exemplary device that may employ the above described processes. The device illustrated is meant for illustrative purposes only and is not meant to be limiting. ICD 500 is an implantable cardioverter defibrillator. It should be appreciated that such a device may include pacing, defibrillation, cardioversion, and/or other therapies alone or in any combination. The leads shown are illustrative, it being noted that other specific forms of leads are within the scope of this invention. Ventricular lead 516 as illustrated has, located adjacent to the distal end, an extendable helix electrode 526 and a ring electrode 524, the helix electrode being mounted retractably within an insulative head 527. Electrodes 524 and 526 are used for bipolar ventricular pacing and for bipolar sensing of ventricular depolarizations. While electrodes 524 and 526, may be used for bipolar pacing and sensing, electrode 526 may be used in conjunction with the surface of device casing 510, which surface acts as a common or indifferent electrode in what is termed unipolar operation. Ventricular lead 516 also carries a coil electrode 520, sometimes referred to as the RV (right ventricular) coil, for delivering defibrillation and/or cardioversion pulses. Coil electrode 520 is positioned on lead 16 so that when the distal tip is at the apex of the ventricle, coil 520 is positioned in the right ventricle. Lead 16 may also carry, optionally, an SVC coil 530, which can be used for applying cardioversion pulses. Lead 516 carries respective concentric coil conductors (not shown), separated from one another by appropriate means such as tubular insulative sheaths and running the length of the lead for making electrical connection between the ICD device 500 and respective ones of electrodes 520, 524, 526 and 530.

Atrial lead 515 as illustrated includes an extendable helix electrode 517 and a ring electrode 521, the helix electrode being mounted retractably within an insulative head 519. Electrodes 517 and 521 are used for bipolar atrial pacing and for sensing atrial depolarizations. While electrodes 517 and 521 may be used for bipolar pacing and sensing, electrode 517 may be used in conjunction with the surface of device casing 510, which surface acts as a common or indifferent electrode in what is termed unipolar operation. Note that, in this example, atrial lead 515 is not equipped with coils for use in the sensing and delivery of cardioversion of defibrillation pulses. This is not meant to preclude the inclusion of such applications that may be used advantageously with the present invention.

An ICD device 500, is shown in combination with atrial and ventricular leads, with the lead connector assembly 513, 514, 518, and 522 being inserted into the connector block 512 of the device 500. A specific example of a defibrillation pulse generator that may be used in conjunction with the present ventricular lead is disclosed in U.S. Pat. No. 4,953,551. Other ICD type units can be used; reference is made to U.S. Pat. Nos. 5,163,427 and 5,188,105 as disclosing illustrative forms of apparatus for delivering cardioversion and defibrillation pulses. As used herein, the term "ICD type" device refers to any device that can apply both pacing therapy and shock therapy for controlling arrhythmias. An implantable medical device (ICD) is a medical device the delivers electrical stimulation and may take the form of a dedicated pacing device, a cardioverting/defibrillation device, an ICD, a neurostimulator, a muscle stimulator, a spinal stimulator, a gastrointestinal stimulator or the like.

Figure 5:
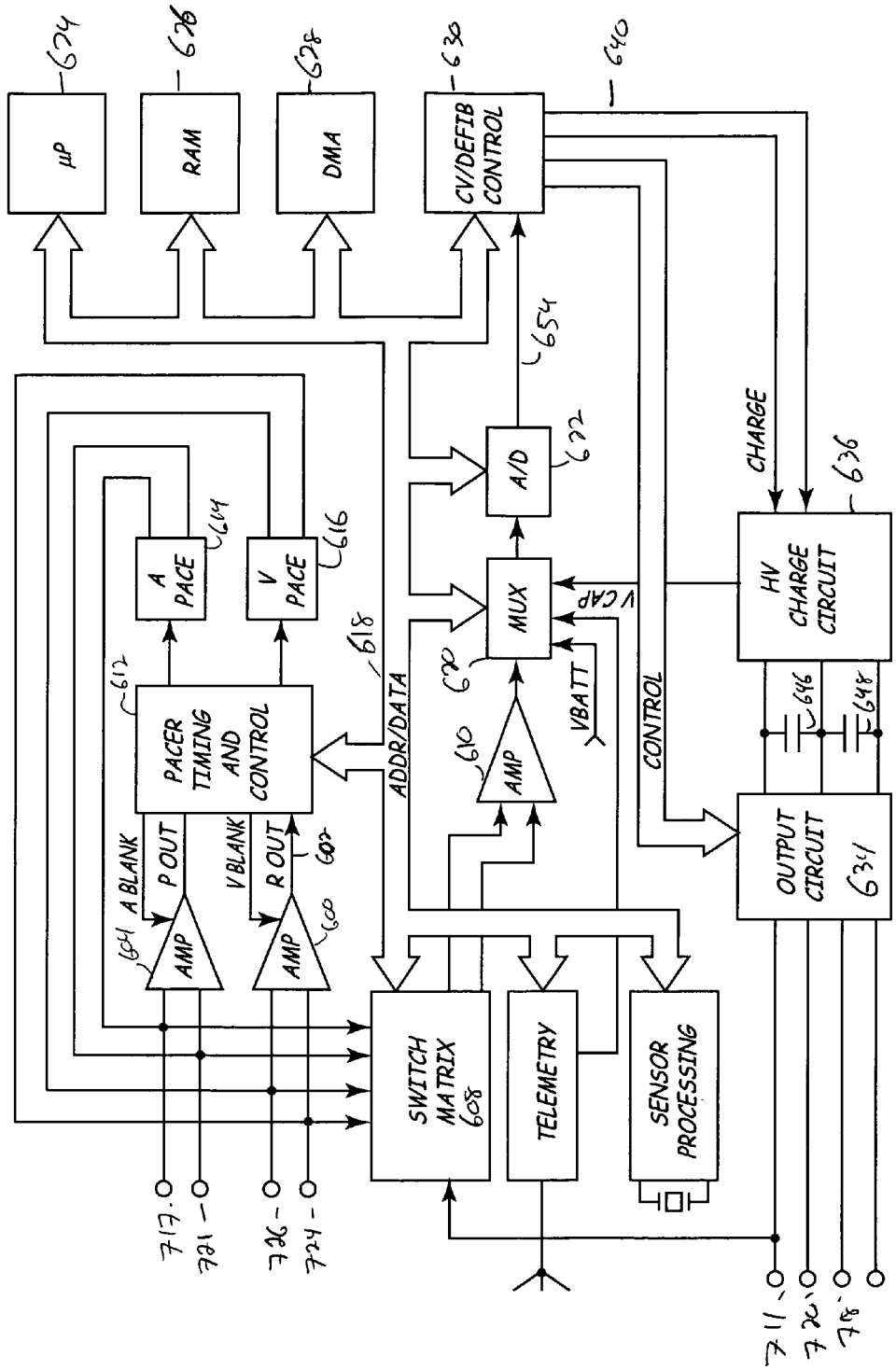
FIG. 5 is a schematic diagram if a circuit for the implantable medical device of FIG. 4.

FIG. 5 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide anti-tachycardia pacing therapies, anti-tachycardia pacers which do not provide cardioversion or defibrillation, and devices which deliver different forms of anti-arrhythmia therapies such as nerve stimulation or drug administration.

The device is provided with a lead system including electrodes, which may be as illustrated in FIG. 3. Alternate lead systems may of course be substituted. If the electrode configuration of FIG. 4 is employed, the correspondence to the illustrated electrodes is as follows. Electrode 711 corresponds to electrode 516, and is the uninsulated portion of the housing of the implantable pacemaker/ cardioverter/defibrillator. Electrode 720 corresponds to electrode 520 and is a defibrillation electrode located in the right ventricle. Electrode 718 corresponds to electrode 530 and is a defibrillation electrode located in the superior vena cava. Electrodes 724 and 726 correspond to electrodes 524 and 526, and are used for sensing and pacing in the ventricle. Electrodes 717 and 721 correspond to electrodes 517 and 521 and are used for pacing and sensing in the atrium.

Electrodes 711, 718 and 720 are coupled to high voltage output circuit 634. Electrodes 724 and 726 are located on or in the ventricle and are coupled to the R-wave amplifier 600, which preferably takes the form of an automatic gain controlled amplifier providing an adjustable sensing threshold as a function of the measured R-wave amplitude. A signal is generated on R-out line 602 whenever the signal sensed between electrodes 724 and 726 exceeds the present sensing threshold.

Electrodes 717 and 721 are located on or in the atrium and are coupled to the P-wave amplifier 604, which preferably also takes the form of an automatic gain controlled amplifier providing an adjustable sensing threshold as a function of the measured P-wave amplitude. A signal is generated on P-out line 606 whenever the signal sensed between electrodes 717 and 721 exceeds the present sensing threshold. The general operation of the R-wave and P-wave amplifiers 500 and 604 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety.

Switch matrix 608 is used to select which of the available electrodes are coupled to wide band (0.5-200 Hz) amplifier 610 for use in signal analysis. Selection of electrodes is controlled by the microprocessor 624 via data/address bus 618, which selections may be varied as desired. Signals from the electrodes selected for coupling to bandpass amplifier 610 are provided to multiplexer 620, and thereafter converted to multi-bit digital signals by A/D converter 622, for storage in random access memory 626 under control of direct memory access circuit 628. Microprocessor 624 may employ digital signal analysis techniques to characterize the digitized signals stored in random access memory 626 to recognize and classify the patient's heart rhythm employing any of the numerous signal-processing methodologies known to the art.

The remainder of the circuitry is dedicated to the provision of cardiac pacing, cardioversion and defibrillation therapies, and, for purposes of the present invention may correspond to circuitry known in the prior art. An exemplary apparatus is disclosed of accomplishing pacing, cardioversion and defibrillation functions follows. The pacer timing/control circuitry 612 includes programmable digital counters which control the basic time intervals associated with DDD, VVI, DVI, VDD, AAI, DDI and other modes of single and dual chamber pacing well known to the art. Circuitry 612 also controls escape intervals associated with anti-tachyarrhythmia pacing in both the atrium and the ventricle, employing any anti-tachyarrhythmia pacing therapies known to the art.

Microprocessor 624 operates as an interrupt driven device, and is responsive to interrupts from pacer timing/control circuitry 612 corresponding to the occurrences of sensed P-waves and R-waves and corresponding to the generation of cardiac pacing pulses. These interrupts are provided via data/address bus 618. Any necessary mathematical calculations to be performed by microprocessor 624 and any updating of the values or intervals controlled by pacer timing/control circuitry 612 take place following such interrupts. A portion of the memory 626 may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

What is claimed is:

1. A method of selecting a threshold testing methodology in a cardiac pacing device having a lead for delivering pacing pulses, the method comprising:

conducting a threshold test utilizing an algorithmic threshold testing methodology and obtaining a first threshold value;

conducting a threshold test utilizing an evoked response methodology and obtaining a second threshold value;

comparing the first threshold value with the second threshold value;

determining that the lead has a high polarization if the second threshold value is less than the first threshold value and precluding the use of the evoked response methodology so long as the lead has high polarization; and determining that the lead has a low polarization if the first threshold value is substantially equal to or less than the second threshold value and permitting the use of the evoked response methodology.

2. The method of claim 1, further comprising re-obtaining values for the first and second threshold values and re-evaluating whether the lead has high polarization or low polarization at the expiration of an evoked response evaluation interval.

3. The method of claim 1, further comprising re-obtaining values for the first and second threshold values and re-evaluating whether the lead has high polarization or low polarization if the evoked response methodology indicates the threshold has changed over time.

4. A method comprising:
   determining if a lead of an implantable medical device has a high polarization or a low polarization, wherein the determining includes:
   obtaining a first threshold value with an algorithmic based methodology and obtaining a second threshold value with the evoked response methodology;
   comparing the first threshold value and the second threshold value; and
   classifying the lead as a low polarization lead unless the second threshold value is less than the first threshold value; and
   using an evoked response methodology for threshold testing only if the lead has a low polarization.

5. The method of claim 4, further comprising:
   repeating the step of determining if the evoked response methodology indicates that a threshold value obtained during the threshold testing has increased.

6. The method of claim 4, further comprising generating an alert if after repeating the step, the lead is determined to have a high polarization.

7. The method of claim 4, further comprising:
   repeating the step of determining at the expiration of an evoked response threshold interval.

8. The method of claim 7, further comprising generating an alert if after repeating the step, the lead is determined to have a high polarization.

9. An implantable medical device (IMD) comprising:
   means for providing cardiac pacing;
   means for determining a polarization of a lead coupled with the means for providing cardiac pacing, wherein the determining includes:
   obtaining a first threshold value with an algorithmic based methodology and obtaining a second threshold value with the evoked response methodology;
   comparing the first threshold value and the second threshold value; and
   classifying the lead as a low polarization lead unless the second threshold value is less than the first threshold value; and
   means for selecting an algorithmic threshold testing methodology or an evoked response threshold testing methodology based upon the determined polarization of the lead.

10. The IMD of claim 9, further comprising means for periodically re-evaluating the polarization of the lead.

11. The IMD of claim 9, further comprising means for re-evaluating the polarization of the lead if the evoked response methodology determines that a threshold value have varied beyond a predetermined amount.

12. The IMD of claim 9, further comprising means for re-evaluating the polarization of the lead and means for communicating a change of polarization from low to high.

* * * * *